United States Patent [19]

Kummer et al.

[11] 4,454,358

[45] Jun. 12, 1984

[54] CONTINUOUS PRODUCTION OF ETHANOL AND PLURAL STAGE DISTILLATION OF THE SAME

[75] Inventors: Rudolf Kummer, Frankenthal; Volker Taglieber, Eppelheim; Heinz-Walter Schneider, Ludwigshafen, all of Fed. Rep. of Germany

[73] Assignee: BASF Aktiengesellschaft, Fed. Rep. of Germany

[21] Appl. No.: 337,683

[22] Filed: Jan. 7, 1982

[30] Foreign Application Priority Data

Jan. 21, 1981 [DE] Fed. Rep. of Germany ....... 3101750

[51] Int. Cl.$^3$ .......................... B01D 3/00; C07C 29/80
[52] U.S. Cl. ..................................... 568/885; 568/902; 203/19; 203/32; 203/38; 203/81; 203/DIG. 6; 203/DIG. 19; 203/28
[58] Field of Search .......... 203/19, DIG. 6, DIG. 13, 203/71, 81, 28, 29, 32, 38, DIG. 19, 74; 568/902, 885, 884, 876, 913, 909, 890

[56] References Cited

U.S. PATENT DOCUMENTS

| | | | |
|---|---|---|---|
| 2,192,489 | 3/1940 | Rosebaugh | 203/71 |
| 2,726,199 | 12/1955 | Birbauer et al. | 203/81 |
| 2,782,243 | 2/1957 | Hess et al. | 568/885 |
| 2,806,816 | 9/1957 | Staib et al. | 203/83 |
| 2,826,536 | 3/1958 | Grekel et al. | 203/83 |
| 4,239,924 | 12/1980 | Pretzer et al. | 568/902 |
| 4,277,634 | 7/1981 | Walker | 568/902 |

FOREIGN PATENT DOCUMENTS 2726928 1/1979 Fed. Rep. of Germany .

OTHER PUBLICATIONS

Ind. Eng. Chem. Prod. Res. Dev., vol. 17/3 (1978), pp. 231 et seq.

*Primary Examiner*—Wilbur L. Bascomb, Jr.
*Attorney, Agent, or Firm*—Keil & Witherspoon

[57] ABSTRACT

Ethanol is produced continuously via the carbonylation of methanol, by
(a) carbonylating methanol, in a reactor R, in the presence of a carbonyl complex of a metal of group VIII of the periodic table and of a halogen compound,
(b) separating, in a distillation column D1, the reactor discharge, into a top fraction comprising methyl acetate, methanol, dimethyl ether and an organohalogen compound, and into a bottom fraction comprising water, small quantities of acetic acid and the catalyst, if the latter is not in a fixed bed, the residence time being so adjusted that the greater part of the acetic acid reacts with the methanol present to give methyl acetate,
(c) separating the top fraction from D1, in a distillation column D2, into a top fraction comprising small quantities of methyl acetate, methanol, dimethyl ether and the organo-halogen compound, and a bottom fraction comprising methyl acetate and methanol, and recycling the top fraction to reactor R,
(d) distilling off, via the top of distillation column D3, the greater part of the water from the bottom fraction from D1 and removing this water from circulation, and recycling to reactor R the bottom fraction consisting of small quantities of water, acetic acid and the catalyst,
(e) using hydrogen to hydrogenate, in the hydrogenation reactor H, the bottom fraction from D2, in a conventional manner, to give a mixture of methanol and ethanol, and
(f) separating the mixture into ethanol and methanol in a distillation column D4, and recycling the methanol to reactor R.

2 Claims, 2 Drawing Figures

H Ac = Essigsäure    Me-O-Me = Dimethylether    Et OH = Ethanol
Me OH = Methanol    Me J = Methyljodid    HS = Höher siedende Nebenprodukte
Me Ac = Methylacetat    Kat = Katalysator    ( ) = geringe Mengen Legende s.Fig.1

CONTINUOUS PRODUCTION OF ETHANOL AND PLURAL STAGE DISTILLATION OF THE SAME

The present invention relates to a new process for the continuous production of ethanol.

It is well known that methanol can be converted to ethanol by various carbonylation methods, for example by one-stage or two-stage homolog formation according to the following equations:

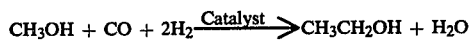

$$CH_3OH + CO + 2H_2 \xrightarrow{\text{Catalyst}} CH_3CH_2OH + H_2O$$

or

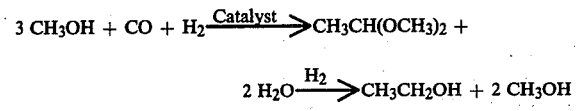

$$3 CH_3OH + CO + H_2 \xrightarrow{\text{Catalyst}} CH_3CH(OCH_3)_2 +$$

$$2 H_2O \xrightarrow{H_2} CH_3CH_2OH + 2 CH_3OH$$

However, recent investigations have shown (Ind. Eng. Chem. Prod. Res. Dev., Volume 17/3 (1978), page 231 et seq. and German Laid-Open Application DOS No. 2,726,978) that these reactions give ethanol yields of only 50 to 60%.

A further possibility of preparing ethanol from methanol is the carbonylation of methanol to methyl acetate, followed by hydrogenation of the methyl acetate:

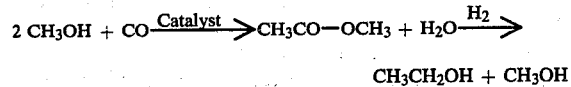

$$2 CH_3OH + CO \xrightarrow{\text{Catalyst}} CH_3CO-OCH_3 + H_2O \xrightarrow{H_2}$$

$$CH_3CH_2OH + CH_3OH$$

However, since the carbonylation of methanol produces, instead of pure methyl acetate, a mixture of methyl acetate, acetic acid, methanol, dimethyl ether, water and, in most cases, also organoiodine compounds and other by-products, this route for ethanol production has not hitherto been used, owing to the considerable process engineering problems.

It was an object of the present invention, in the face of the prejudice based on the above reasoning, to make the carbonylation of methanol for the production of ethanol industrially and economically feasible.

We have found that this object is achieved by a continuous process for the production of ethanol via the carbonylation of methanol, which comprises (a) carbonylating methanol in a manner which is known per se, in a reactor R, in the presence of a carbonyl complex of a metal of group VIII of the periodic table and of a halogen compound as activator, (b) separating, in a distillation column D1, the reactor discharge, which essentially consists of methyl acetate, methanol, acetic acid, water and small quantities of dimethyl ether, methyl iodide and the catalyst, if the latter is not in a fixed bed, into a top fraction comprising methyl acetate, methanol, dimethyl ether and an organo-halogen compound, and a bottom fraction comprising water, small quantities of acetic acid and the catalyst, the residence time being so adjusted that the bulk of the acetic acid reacts with the methanol present to give methyl acetate, (c) separating the top fraction from D1, in a distillation column D2, into a top fraction comprising small quantities of methyl acetate, methanol, dimethyl ether and the organo-halogen compound, and a bottom fraction comprising methyl acetate and methanol, and recycling the top fraction to reactor R, (d) distilling off, via the top of distillation column D3, the greater part of the water from the bottom fraction from D1 and removing this water from circulation, and recycling to reactor R the bottom fraction consisting of small quantities of water, acetic acid and the catalyst, (e) using hydrogen to hydrogenate, in the hydrogenation reactor H, the bottom fraction from D2, in a conventional manner, to give a mixture of methanol and ethanol, and (f) separating the mixture into ethanol and methanol in a distillation column D4, and recycling the methanol to reactor R.

Figure 1:
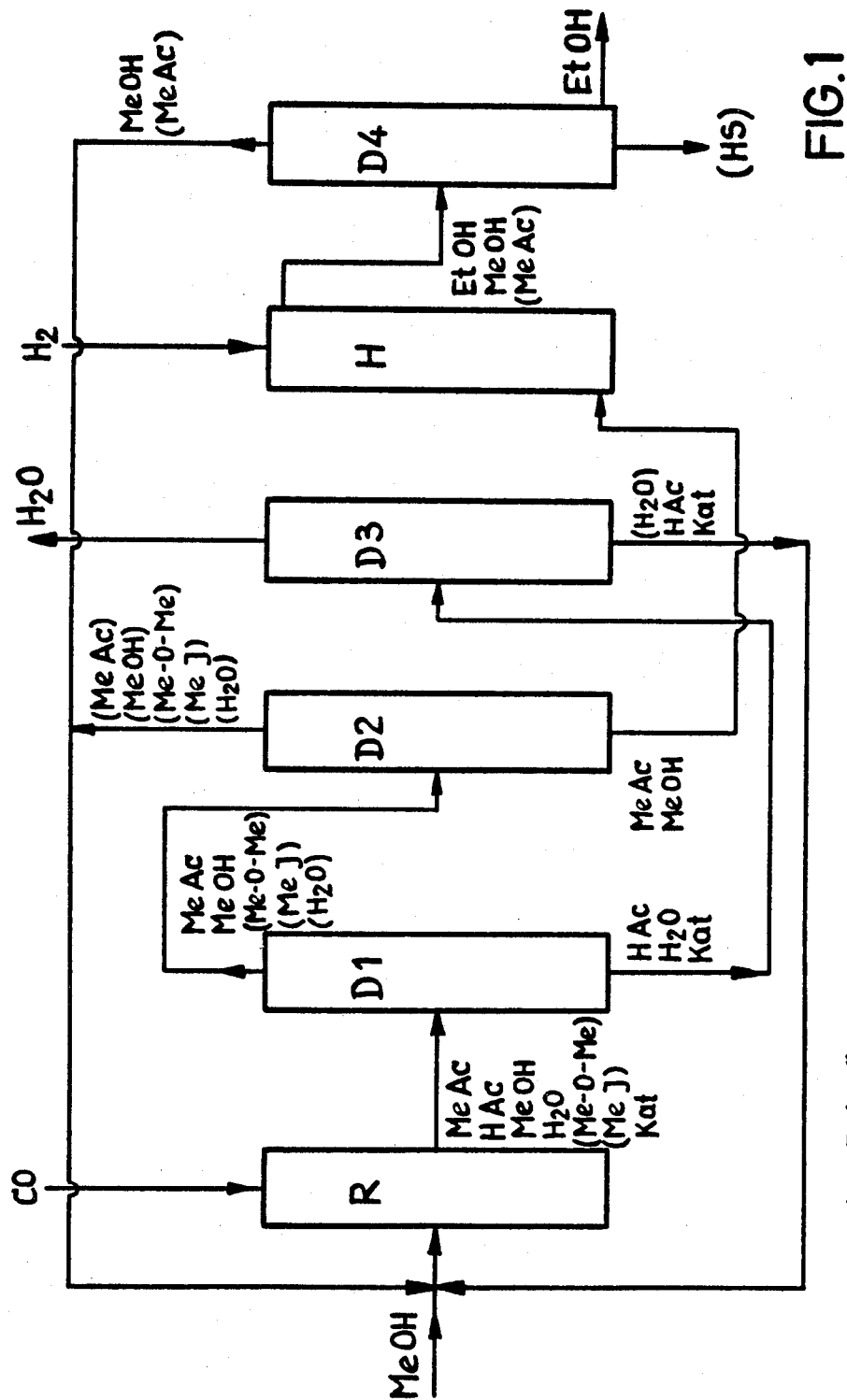
FIG. 1 is self-explanatory in the light of the above description and constitutes the flow sheet for the case in which an iodide is used as the activator, methyl iodide being principally obtained as the organohalogen compound.
Figure 2:
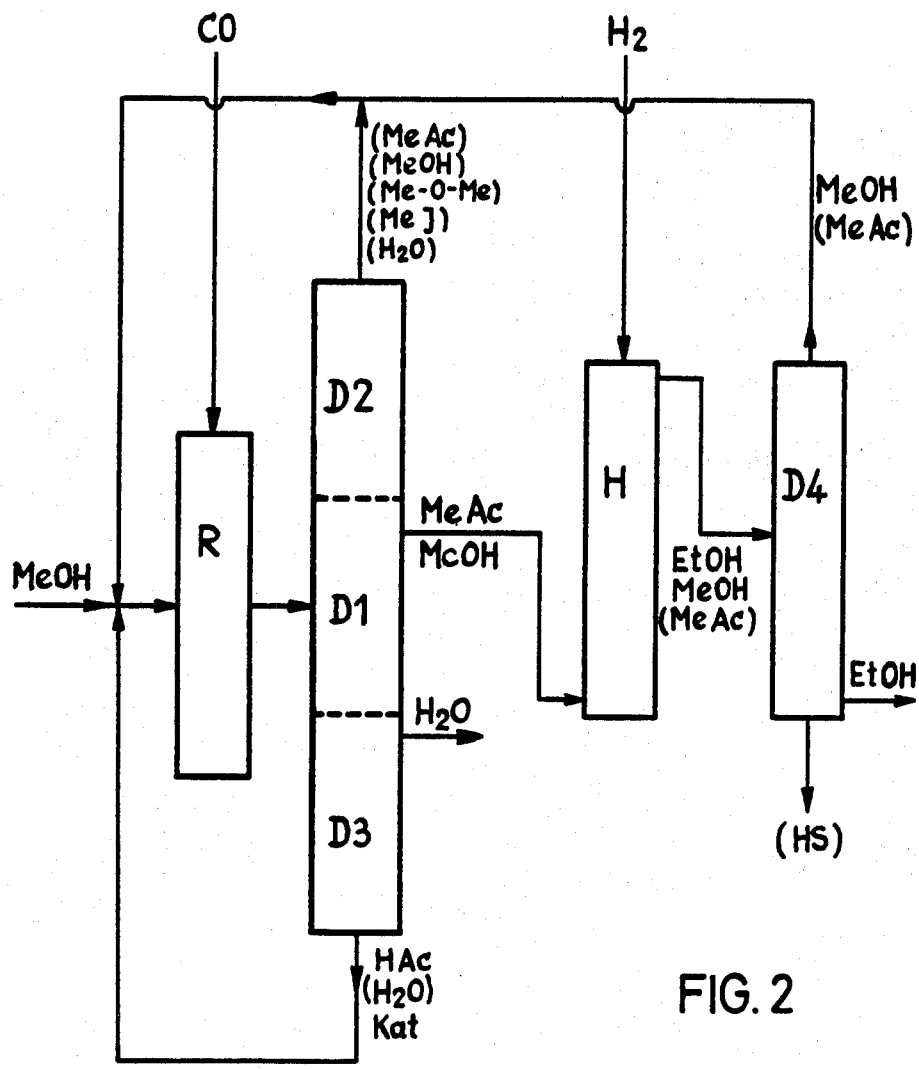
FIG. 2 shows an alternative apparatus for this process, in which the functions of the distillation columns D1, D2 and D3 are combined in a single column, the methyl acetate/methanol fraction and the water fraction being taken off as side streams.

Many versions of process step (a), namely the carbonylation of methanol, are known. In general, this step is carried out at from 50° to 300° C. and under a CO pressure of from 1 to 800 bar, in the presence of a catalyst comprising a carbonyl complex of a metal of group VIII of the periodic table and in the presence of a halogen compound as an activator.

Central atoms in the catalysts are cobalt, nickel and particularly rhodium. In addition, it is advantageous to use, instead of the pure, relatively unstable carbonyl complexes, those in which a part of the CO ligands have been replaced by other ligands to increase the stability of the complexes. As is known, such ligands are, in particular, organic compounds of trivalent phosphorus, such as $C_4$-$C_{12}$-trialkylphosphines and phosphites, and triarylphosphines and phosphites, triphenylphosphine being particularly preferred.

Although it is possible to use a ready-prepared complex, eg. $Rh(CO)(PPh_3)_2Cl$ (Ph=phenyl), it is generally more economical and technically simpler to start with the salts of the appropriate metals, with or without the ligands, since the complexes are formed in situ under the reaction conditions.

From $10^{-4}$ to 1 gram atom of the catalyst metal should advantageously be present in the reactor per kilogram of methanol, and the quantity of ligands is advantageously from 2 to 100 moles per gram atom of metal. The molar excess of the ligand serves to shift the balance in favor of the mixed complexes; this balance otherwise tends to the side of the pure carbonyl complexes, owing to the large amount of CO available.

As is known, halogen compounds such as chlorides, bromides and especially iodides are suitable activators and can be used, for example, as salts, eg. LiI or NaI, or in the form of hydrohalic acids. During the reaction, organic halides, particularly methyl halides, are formed from these halogen compounds, methyl iodide being formed in most cases in practice, owing to the preferred use of iodine. The quantity of these activators is preferably from $10^{-2}$ to $10^{-3}$ mole of halogen per gram atom of the catalyst metal.

Solvents may be present but are generally not required. Suitable solvents are acetic acid, higher carboxylic acids, high-boiling carboxylates and hydrocarbons which boil at above 100° C.

In general, it is advisable to limit the conversion of methanol to about 50–80%, since by-products are formed to an increased extent at higher degrees of conversion. If these by-products are formed, they have to be removed in a conventional manner from circulation, in particular—since they are higher-boiling than the other components—from the bottom product of column D3; for clarity, this stream has not been represented in the figures. To what extent the advantage of the higher methanol conversion compensates for the disadvantage of the increased extent of formation and removal of by-products is a question of conventional cost-efficiency optimization, which depends on the circumstances of the particular case.

Based on a methanol conversion of 100%, the carbonylation gives about 10–50% of methyl acetate, 5–40% of acetic acid, 5–20% of dimethyl ether, 5–10% of water and small quantities of other products, such as ethanol, propionic acid and propionates.

Within the scope of the novel process, it is particularly advantageous to carry out the carbonylation in the liquid phase at from 150° to 200° C. and from 5 to 50 bar, over an Rh/triphenylphosphine catalyst with an iodide as the activator. The quantity of rhodium in the catalyst is from $10^{-3}$ to $10^{-1}$% by weight, based on the methanol present in the reactor, the quantity of triphenylphosphine is from 5 to 100 moles per gram atom of rhodium and the quantity of iodide, employed as hydrogen iodide or methyl iodide, is from 10 to 100 moles of I per gram atom of rhodium. The methanol conversion is restricted to 70–80%, so that the reactor discharge is a mixture comprising from 35 to 50% by weight of methyl acetate, from 5 to 20% by weight of methanol, from 5 to 15% by weight of acetic acid, from 5 to 20% by weight of water, from 1 to 15% by weight of dimethyl ether, up to 5% by weight of other products and the residual catalyst constituents. The space-time yield for the desired products methyl acetate and acetic acid is from about 0.1 to 0.6 kg/l/hour for the preferred embodiment of the carbonylation step of the novel process.

However, the carbonylation can also be carried out in the gas phase, in a manner which is known per se, over a fixed catalyst. In this case, the circulated material does not contain a metallic catalyst constituent.

The reaction mixture obtained by process step (a) is then fed, in accordance with process step (b), to distillation column D1. This column has the function of separating off the low-boiling constituents, namely methyl acetate, methanol, dimethyl ether and methyl iodide, from the higher-boiling constituents, and of esterifying the available acetic acid with the methanol, which is present in a molar excess, to give methyl acetate. Since the methyl acetate is continuously removed from the equilibrium, the esterification proceeds unrestricted provided that average residence times of from 5 to 30 minutes are maintained for the reactants in column D1. The average residence times can be selected by means of the reflux ratio and/or by means of adjustment of the height of the weir at the bubble-cap trays or trays of similar construction. In most cases, however, simple packed columns are adequate. It is advantageous to maintain a degree of esterification of 60–80%, since the residual acetic acid facilitates the circulation of catalyst.

The number of separation stages in D1 is advantageously from 5 to 15 theoretical plates.

In process step (c), the top fraction from D1 is separated, in distillation column D2, into a top fraction, comprising a smaller quantity, of dimethyl ether, methyl iodide and lesser proportions of methanol and methyl acetate and a bottom fraction of methanol and methyl acetate. The columns used for this purpose are of any desired construction—for economic reasons, packed columns are preferably used—and have about 10–20 theoretical plates. The top fraction from D2 is then immediately recycled to the reactor R, since dimethyl ether behaves like methanol in the carbonylation.

The bottom fraction from D1 is fed, in accordance with process step (d), to column D3, in which the greater part of the water which is formed continuously during the carbonylation and the esterification is removed from circulation. The bottom fraction, which contains the residual water, a small quantity of acetic acid and the catalyst components (the metal complex with or without the excess ligands), is recycled to the reactor R. If higher-boiling carbonylation products are also present, they are removed either as a side-stream from D3 and/or in a continuous or batchwise additional operation at a point between the bottom of D3 and the reactor R. This type of operation, which is necessary from time to time to regenerate the catalyst, corresponds to the conventional technique of a continuous process with closed circuit materials and therefore requires no further discussion.

Column D3 has about 5 to 15 theoretical plates and is of any desired construction, so that a packed column is also advantageously used in this case.

In process step (e), the bottom product of D2, which product consists predominantly of methyl acetate and methanol, is hydrogenated in a manner which is known per se, in hydrogenation reactor H, to give a mixture of methanol and ethanol. For this process, it is preferable to use a copper/chromite catalyst (Adkins catalyst) or a copper oxide catalyst, at a hydrogen pressure of 100–300 bar and at about 180°–250° C. This hydrogenation proceeds smoothly but care must be taken to ensure as complete a conversion as possible, so that it does not stop, in part, at intermediates such as aldehydes, acetals, ethers and esters. The space-time yield in the hydrogenation is about 0.5–1.0 kg/l/hour.

In process step (f), which is also carried out in a manner which is known per se, the reaction mixture obtained in reactor H is separated into its components. The distillation column D4 used for this purpose can be of any desired construction (a packed column is preferably used) and should have about 15–25 theoretical plates. Higher-boiling products, which are formed in the course of the process and are entrained as far as D4, are removed as a bottom product. The top fraction is methanol, which can still contain a small quantity of methyl acetate. This top product is recycled to the synthesis stage.

Ethanol is obtained as a product of technical-grade purity (99%) and in a yield of from 95 to 96%, based on methanol used, and is taken off as a liquid or vapor side stream from column D4.

All distillation steps can be carried out under atmospheric pressure or—for greater ease of cooling—under slightly superatmospheric pressure.

The novel process not only gives high ethanol yields but solves, in a technically particularly elegant manner, the problem of working up carbonylation mixtures. In particular, the frequently difficult separation, regeneration and recycling of all catalytic substances are effected, in a technically particularly simple and economical manner, by circulation according to the invention.

EXAMPLE

Ethanol was prepared in a pilot plant according to FIG. 1, and although the individual steps up to the hydrogenation were carried out batchwise, in their entirety they represented a model experiment for a subsequent continuous operation. The values given are from the 5th cycle of an experiment repeated a total of 7 times to achieve a pseudo-steady state.

In this state, the quantities of material remaining in the reactors and columns were no longer taken into account.

(a) Carbonylation in reactor R

The carbonylation was carried out in a shaken tantalum autoclave R of 1 liter capacity, under a CO pressure of 40 bar at 175° C., in the course of 1 hour, in the presence of an Rh/I/triphenylphosphine catalyst system.

The mixtures of starting materials had the following composition:

|  | fresh | recycled | total |
|---|---|---|---|
| Methanol | 138 g | 204 g | 342 g |
| Methyl acetate | — | 35 g | 35 g |
| Acetic acid | — | 12 g | 12 g |
| Dimethyl ether | — | 49 g | 49 g |
| Water | — | 17 g | 17 g |
| Rh catalyst | — | 2 g | 2 g |
| PPh3 (Ph = phenyl) | — | 2 g | 2 g |
| CH3I | — | 32 g | 32 g |

The complex Rh(CO)(PPh3)2Cl was used as the Rh catalyst; the ratio of Rh to methanol was $7.10^{-3}$ mole per kg, the molar ratio of free PPh3 to Rh was 4:1 and the molar ratio of I to Rh was 100:1.

The iodine was initially employed as aqueous hydriodic acid and in the recycled form was present virtually entirely as methyl iodide.

The reactor discharge had the following composition:

| Methyl acetate | 238 g |
|---|---|
| Acetic acid | 99 g |
| Dimethyl ether | 51 g |
| Methanol | 123 g |
| Water | 70 g |
| Catalyst constituents | 4 g |
| Other products (CH3I etc) | 35 g |
| Total | 620 g |

This corresponds to a methanol conversion of 64.0%, the selectivity being about 65% with respect to methyl acetate and about 35% with respect to acetic acid. Dimethyl ether, which was recycled and formed in the same amounts, was not taken into consideration.

(b) Distillation in D1

The reactor discharge was separated, under atmospheric pressure, in a 1.8 m high packed column D1 which had about 20 theoretical plates, into two fractions of the following compositions:

| Top fraction | |
|---|---|
| Methyl acetate | 343 g |
| Dimethyl ether | 49 g |
| Methanol | 77 g |
| Methyl iodide | 32 g |
| Water | 1 g |
| Total | 502 g |
| Bottom fraction | |
| Acetic acid | 12 g |
| Water | 95 g |
| Catalyst constituents | 4 g |
| Other products | 3 g |
| Total | 114 g |

The degree of esterification of acetic acid with methanol to give methyl acetate was 87.5%.

(c) Distillation in D2

The top fraction from D1 was separated, under atmospheric pressure, in a 1.8 m high packed column D2 which had about 20 theoretical plates, into the following two fractions:

| Top fraction | |
|---|---|
| Methyl acetate | 22 g |
| Dimethyl ether | 49 g |
| Methanol | 5 g |
| Methyl iodide | 32 g |
| Water | 1 g |
| Total | 109 g |
| Bottom fraction | |
| Methyl acetate | 321 g |
| Methanol | 71 g |
| Total | 392 g |

(d) Distillation in D3

The bottom fraction from D1 was separated, under normal pressure, in a 1.2 m high packed column D3 which had about 10 theoretical plates, into the following fractions:

| Top fraction | |
|---|---|
| Water | 79 g |
| Bottom fraction | |
| Water | 16 g |
| Acetic acid | 12 g |
| Catalyst constituents | 4 g |
| Other products | 3 g |
| Total | 35 g |

(e) Hydrogenation in H

The hydrogenation of the bottom fraction from D2 in a 2.0 l reactor was carried out continuously at 190° C. and under a hydrogen pressure of 280 bar, at a throughput of 500 g of methyl acetate per hour per liter of fixed bed catalyst. The commercial catalyst used consisted of tablets of 5 mm diameter and 3 mm thickness, which loosely filled the reactor and had the following composition in % by weight: 34.4% of SiO2; 36.0% of CuO; 17.2% of MgO; 1.0% of BaO; 1.1% of Cr2O3 and 0.6% of ZnO.

The reactor discharge consisted of:

| Ethanol | 189 g |
|---|---|
| Methanol | 199 g |
| Methyl acetate | 13 g |
| Other products | 3 g |
| Total | 404 g |

This corresponded to 96.1% hydrogenation of the methyl acetate, the selectivity being 99.0% with respect to ethanol.

(f) Distillation in D4

The discharge from the hydrogenation reactor was separated, under normal pressure in a 4 m high bubble-cap tray column which had about 15 theoretical plates, into the following fractions:

| Top fraction | |
|---|---|
| Methanol | 199 g |
| Methyl acetate | 13 g |
| Total | 212 g |

Side stream taken off at the height of the 3rd tray from the bottom

| Ethanol | 189 g |
|---|---|
| Bottom fraction | |
| Higher-boiling constituents | 0.4 g |

The yield of ethanol was thus about 40%, based on the total methanol employed in reactor R. The selectivity with respect to ethanol was 95.5%, based on methanol initially fed in.

The top fractions from D2 and D4 and the bottom fraction from D3 were recycled to the reactor R, together with the appropriate quantities of fresh starting materials, and were subjected to a further experimental cycle. When this cycle was repeated several times, the qualitatively and quantitatively virtually constant balance shown above was established.

We claim:

1. A process for the continuous production of ethanol via the carbonylation of methanol, which comprises
   (a) carbonylating methanol with carbon monoxide in a reactor R, in the presence of a carbonyl complex of a metal of group VIII of the periodic table which complex is dispersed in the liquid reaction medium, and in the presence of a halogen compound as activator;
   (b) separating, in a distillation column D1, the reactor discharge, which essentially consists of methyl acetate, methanol, acetic acid, water and small quantities of dimethyl ether, an organo-halogen compound and the catalyst, into a top fraction comprising methyl acetate, methanol, dimethyl ether and the organo-halogen compound, and into a bottom fraction comprising water, small quantities of acetic acid and the catalyst, the residence time of the discharge in column D1 being so adjusted that the bulk of the acetic acid reacts with the methanol present to give methyl acetate;
   (c) separating the top fraction from D1, in a distillation column D2, into a top fraction comprising small quantities of methyl acetate, methanol, dimethyl ether and the organo-halogen compound, and a bottom fraction comprising methyl acetate and methanol and recycling the top fraction to reactor R;
   (d) distilling off, via the top distillation column D3, the greater part of the water from the bottom fraction from D1 and removing this water from circulation, and recycling to reactor R the bottom fraction consisting of small quantities of water, acetic acid and the catalyst;
   (e) using hydrogen to hydrogenate, in a hydrogenation reaction H, the bottom fraction from D2, to give a mixture of methanol and ethanol, and
   (f) separating the mixture into ethanol and methanol in a distillation column D4, and recycling the methanol to reactor R.

2. A process for the continuous production of ethanol via the carbonylation of methanol, which comprises
   (a) carbonylating methanol with carbon monoxide in a reactor R, in the presence of a carbonyl complex of a metal of group VIII of the periodic table in the form of a fixed catalyst bed and of a halogen compound as activator;
   (b) separating, in a distillation column D1, the reactor discharge, which essentially consists of methyl acetate, methanol, acetic acid, water and small quantities of dimethyl ether, and an organo-halogen compound into a top fraction comprising methyl acetate, methanol, dimethyl ether and the organo-halogen compound, and into a bottom fraction comprising water, and small quantities of acetic acid, the residence time of the discharge in column D1 being so adjusted that the bulk of the acetic acid reacts with the methanol present to give methyl acetate;
   (c) separating the top fraction from D1, in a distillation column D2, into a top fraction comprising small quantities of methyl acetate, methanol, dimethyl ether and the organo-halogen compound, and a bottom fraction comprising methyl acetate and methanol and recycling the top fraction to reactor R;
   (d) distilling off, via the top distillation column D3, the greater part of the water from the bottom fraction from D1 and removing this water from circulation, and recycling to reactor R the bottom fraction consisting of small quantities of water, and acetic acid;
   (e) using hydrogen to hydrogenate, in a hydrogenation reactor H, the bottom fraction from D2, to give a mixture of methanol and ethanol, and
   (f) separating the mixture into ethanol and methanol in a distillation column D4, and recycling the methanol to reactor R.

* * * * *